(12) United States Patent
Lornell

(10) Patent No.: US 8,187,247 B2
(45) Date of Patent: May 29, 2012

(54) MULTI-CONFIGURABLE ABSORBENT ARTICLE

(75) Inventor: Per Lornell, Bollebygd (SE)

(73) Assignee: SCA Hygiene Products AB, Gothenburg (SE)

( * ) Notice: Subject to any disclaimer, the term of this patent is extended or adjusted under 35 U.S.C. 154(b) by 664 days.

(21) Appl. No.: 12/158,242

(22) PCT Filed: Dec. 19, 2005

(86) PCT No.: PCT/EP2005/013655
§ 371 (c)(1),
(2), (4) Date: Jun. 19, 2008

(87) PCT Pub. No.: WO2007/071267
PCT Pub. Date: Jun. 28, 2007

(65) Prior Publication Data
US 2008/0319412 A1    Dec. 25, 2008

(51) Int. Cl.
*A61F 13/15* (2006.01)
(52) U.S. Cl. ............. 604/392; 604/385.3; 604/389
(58) Field of Classification Search .......... 604/389–392, 604/385.3
See application file for complete search history.

(56) References Cited

U.S. PATENT DOCUMENTS

| | | | |
|---|---|---|---|
| 3,265,765 A | 8/1966 | Holden et al. | |
| 3,562,356 A | 2/1971 | Nyberg et al. | |
| 3,700,633 A | 10/1972 | Wald et al. | |
| 4,051,854 A | 10/1977 | Aaron | |
| 4,116,917 A | 9/1978 | Eckert | |
| 4,156,673 A | 5/1979 | Eckert | |
| 5,545,158 A * | 8/1996 | Jessup | 604/385.3 |
| 5,624,428 A * | 4/1997 | Sauer | 604/391 |
| 6,572,601 B2 * | 6/2003 | Suprise et al. | 604/391 |
| 7,217,262 B2 * | 5/2007 | Nakahata et al. | 604/391 |
| 7,347,848 B2 * | 3/2008 | Fernfors | 604/392 |
| 7,527,618 B2 * | 5/2009 | Benning et al. | 604/392 |
| 2001/0034512 A1 * | 10/2001 | Karlsson et al. | 604/392 |

(Continued)

FOREIGN PATENT DOCUMENTS

DE    10 2004 048 540    4/2006

(Continued)

OTHER PUBLICATIONS

An English Translation of the Decision on Grant issued in corresponding Russian Application No. 2008129768.

(Continued)

*Primary Examiner* — Lynne Anderson
(74) *Attorney, Agent, or Firm* — Buchanan Ingersoll & Rooney PC

(57) ABSTRACT

An absorbent article is provided with closure means for securing the article about the waist of a wearer. The article may be worn in a belt type configuration or a slip type configuration. Belt means are provided which are maintained in a retracted position along a rear panel of the article. Releasable attachment means allow the belt to be extended partially or fully. Fasteners on the front panel may be secured to the respective belt means in a slip type configuration, in which the belt means are in a partially or fully retracted configuration. A belt type configuration may be created in a fully extended configuration of the respective belt portions, in which the belt ends may be fastened to each other about the waist of a wearer. The article may have a substantially constant or same size in both the slip or belt type configurations.

20 Claims, 6 Drawing Sheets

U.S. PATENT DOCUMENTS

| | | |
|---|---|---|
| 2002/0193776 A1 | 12/2002 | Fernfors |
| 2004/0092903 A1 | 5/2004 | Olson et al. |
| 2004/0236304 A1 | 11/2004 | Coates et al. |

FOREIGN PATENT DOCUMENTS

| | | |
|---|---|---|
| EP | 0 528 282 A2 | 2/1993 |
| EP | 0 605 014 | 7/1994 |
| EP | 1 110 529 A1 | 6/2001 |
| RU | 2 240 095 | 11/2004 |
| WO | WO 84/04242 | 11/1984 |
| WO | WO 95/19753 A1 | 7/1995 |
| WO | WO 01/21120 A1 | 3/2001 |
| WO | WO 01/74283 A1 | 10/2001 |
| WO | WO 03/017902 A1 | 3/2003 |
| WO | WO 03/017904 A1 | 3/2003 |
| WO | WO 2005/007052 A1 | 1/2005 |
| WO | WO 2006/037595 A1 | 4/2006 |
| WO | WO 2007/071267 A1 | 6/2007 |

OTHER PUBLICATIONS

Form PCT/ISA/210 (International Search Resort dated Jun. 8, 2006.
Form PCT/ISA/237 (Written Opinion of the ernational Searching Autthority) dated Jun. 8, 2006.

International Search Report, Written Opinion and International Preliminary Report on Patentability (Forms PCT/ISA/210, 237 and PCT/IPEA/409) in Application No. PCT/EP2005/013656, dated Sep. 13, 2006.

International Preliminary Report on Patentability and Written Opinion (Forms PCT/IB/326, 373 and PCT/ISA/237) in Application No. PCT/EP2005/013655, dated Jul. 3, 2008.

Per Lornell et al., "Multi-Configurable Absorbent Article" U.S. Appl. No. 12/086,434 dated Jun. 12, 2008.

* cited by examiner

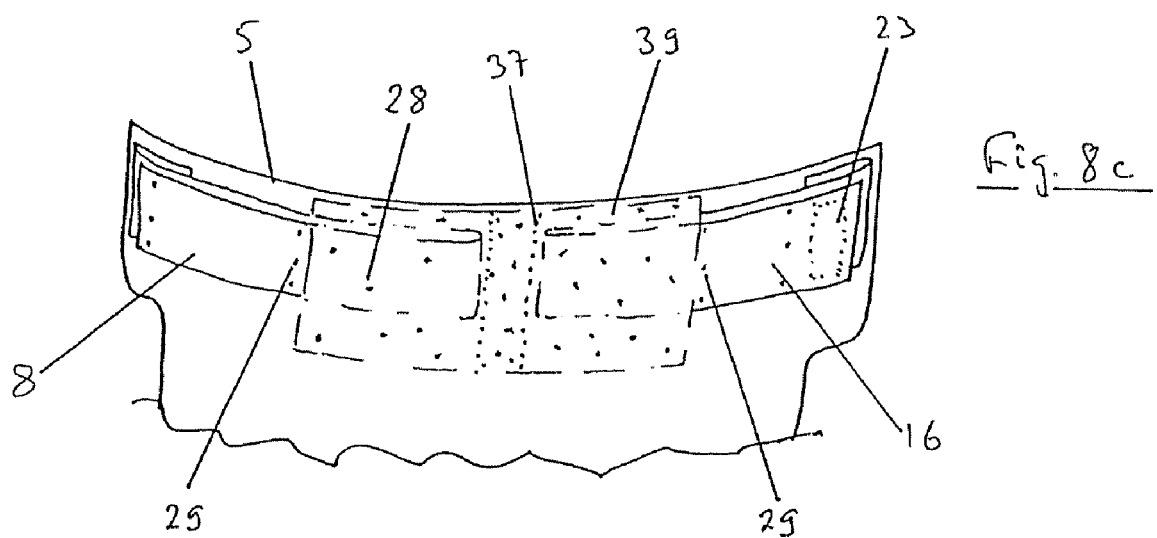

MULTI-CONFIGURABLE ABSORBENT ARTICLE

TECHNICAL FIELD

The present disclosure relates to absorbent articles. In the present context, the term: "absorbent article", is intended to include any absorbent article useful in the field of personal hygiene. The absorbent article of the present disclosure is particularly intended to be a diaper-type article for use by infants, young children or adults for the containment, control and absorption of liquid or solid bodily waste, although other applications or uses of the product may readily be envisaged.

BACKGROUND

In published patent application WO 03/017902, an absorbent article, such as a diaper, is disclosed, in which a front region, a crotch region and a rear region may be attached to a wearer by means of belt members and fasteners. In particular, two belt members, each one projecting laterally outwardly from the rear region of the article, may be joined to each other about the waist of a wearer. Fasteners provided on an inside surface of the front region then ensure that the front region may be secured to the belt, to thereby generate a pant-like garment about the wearer. Another example of a belt-type absorbent product is described in US patent application publication US2002/0193776, in which a belt is provided having a first and a second portion, each of which may be restrained on an inside surface of the article in a retracted position by releasable attachment means.

A further absorbent article is described in document WO 95/19753. According to this document, a diaper type garment is provided with belt members projecting laterally from the rear panel of the garment, each belt member having attachment means at its distal end for connection of a respective belt member about the waist of a wearer, to either the other belt member, or to corresponding attachment portions provided on an outer surface of the front panel of the garment. In this way, the garment may be configured for use in either a slip-type configuration, (sometimes known as a brief-type configuration), in which the distal end of each belt member is drawn part-way about the waist of a wearer and attached to a corresponding portion of the front panel, or in a belt-type configuration, in which the respective ends of the belts are connected together about the waist of a wearer, with the front panel being subsequently secured to the belt by means of fasteners at its lateral edges. As can readily be seen from WO 95/19753 however, a discrepancy arises in the sizing of the garment, when it is worn in one or the other configuration. Specifically, owing to the bridging effect of the front panel between the respective ends of the belt, in the slip-type configuration of the garment, the slip-type configuration generates a larger waist circumference than the belt-type configuration of the same article. A poor fit of the article ensues, unless multiple sizes are stored for a single user, in case of use in one or other configuration. In addition, the lateral edges of the front panel may be unrestrained in the slip-type configuration of the product, which may invite instability of the lateral portions of the front panel and consequent leakage, especially in case of an active wearer.

Also known in the art are diapers which may be provided in a so-called slip-type configuration only, in which, as mentioned, side panels of the article are attached to each other about the waist of a wearer. U.S. Pat. No. 4,051,854 discloses a closure means for an absorbent article which may be provided either on a slip-type garment or on a belt-type garment.

A further absorbent article is known from EP-A-1110529, which is described as comprising a belt attached to a rear panel of the article. The belt is restrained in a storage position by means of releasable attachments, and may be deployed for use by releasing the respective releasable attachments. In use, the two free belt portions, projecting either side of the rear panel, may be joined together enclosing the waist of a wearer and also enclosing the front panel of the article, on which fastener means are applied. Alternatively, the article may be worn in a slip-type configuration, by connecting the belt ends to the outer surface of the front panel. Since, in both cases, the belts must be fastened when in a fully extended condition of the belts, there exists a sizing discrepancy between the belt-type and the slip-type configuration, because of the bridging effect of the front panel. EP-A-0528282 discloses a diaper type article having belt portions projecting from each lateral side of a rear panel. The article is intended to be worn in a belt-type configuration, by joining the belt portions about the waist of a wearer and bringing the front panel into position by means of fasteners on the lateral edges of the front panel which are secured against portions of the belt around the external side of the rear panel of the article. The front and rear panels are generously proportioned in their lateral dimensions and overlap each other substantially when the article is worn. In some cases, the front panel may be fastened against the rear panel without first fastening the belt portions to each other. In such a case the belt portions would lie on the inside of the rear panel causing discomfort and a poor fit.

WO 01/21120 discloses an absorbent article which has a crotch portion between a front and a rear panel. The rear portion, at its lateral side regions, is provided with laterally projecting attachment flaps which may respectively be fastened to side regions of the front panel in order to configure the article in a slip-type configuration for wear. The flaps are formed as belt portions of a continuous belt which is attached to the internal surface of the rear panel and which comprises folds, for allowing a certain extensibility of the belt length within the rear panel against an elastic bias. The garment described can be worn only in a slip-type configuration.

The design feature in the art, according to which absorbent articles may be worn in either a belt-type or a slip-type configuration, has been developed in order to accommodate different end-user requirements and preferences. Nevertheless, in each of the known articles of this type, a size discrepancy exists between the two configurations of the product. Such a size discrepancy may conceivably be compensated for by the use of elastics, although in such a case, the product will tend to be tighter in the belt-type configuration, thereby causing discomfort to a wearer.

Many users of absorbent articles may have limited physical strength and limited dexterity. Configuration and application of such articles can be problematic in terms of the force requirements needed to configure the article, and also the directions in which respective forces are to be applied. In addition, the limb movement of a wearer or user, when applying a force (e.g. opening or closing the garment), need to be taken into account when designing absorbent articles, because certain limb actions are more difficult to perform than others, when applying a force.

There is a need for an absorbent article of the above-mentioned type, which may be configured in a flexible manner, which does not cause discomfort, and wherein the sizing is substantially the same, irrespective of the manner in which the article is configured. There is furthermore a need to provide additional constructional flexibility of absorbent articles, while maintaining material costs at a minimum level. There is furthermore a need to provide an absorbent article which allows easier configuration for use by users. Users of the articles include wearers of the articles and also carers for those who wear the absorbent articles.

In addition, there is a need to keep material usage of such articles to a minimum, for reasons of cost, and in order to reduce the bulkiness of the articles on a wearer. Furthermore, there can be an advantage from reducing the surface area of a wearer which is covered by the article, because prolonged contact between such articles and the skin of a wearer may in some cases cause irritation and discomfort. In devising such articles, care needs to be taken to ensure that the article construction takes into account the needs for comfort and good fit on a wearer.

SUMMARY

The present disclosure sets out to provide an improved absorbent article. In particular, embodiments of the present invention provide an improved absorbent article which addresses the various aspects mentioned above.

In this regard, embodiments of the present invention provide an absorbent article having a topsheet, a backsheet and an absorbent core therebetween; said absorbent article comprising a body panel having a longitudinal axis extending in a longitudinal direction and a transverse axis extending in a lateral direction, said body panel further comprising a crotch region between a front panel and a rear panel, said crotch region and said front and rear panels each having an interior face and an exterior face; said absorbent article including a belt having a first belt portion and a second belt portion; said first and second belt portions each having a distal portion extending laterally from a respective connection region, at which connection region, said belt portion is joined to said rear panel; a belt fastener being provided near a distal end of at least one of said belt members which fastener is capable of securing said first and second belt members to each other about the waist of a wearer; wherein a releasable attachment is provided in association with each respective said first and said second belt portion which, when in an attached condition, secures said belt portions in a retracted configuration, in which retracted configuration a distal region of each said belt portion is releasably restrained directly or indirectly against said exterior face of said rear panel and whereby upon release of said releasable attachment, an extended configuration of respective said belt portion is formed, wherein in which extended configuration, said belt portions may be joined to one-another by means of said belt fastener.

In other words, an absorbent article is provided with closure means for securing the article about the waist of a wearer. The article may be worn in a belt type configuration or a slip type configuration. Belt means are provided which are maintained in a retracted position along a rear panel of the article. Releasable attachment means allow the belt to be extended partially or fully. Fasteners on the front panel may be secured to the respective belt means in a slip type configuration, in which the belt means are in a partially or fully retracted configuration. A belt type configuration may be created in a fully extended configuration of the respective belt portions, in which the belt ends may be fastened to each other about the waist of a wearer. The article may have a substantially constant or same size in both the slip or belt type configurations.

The term "belt", as claimed is to be understood to mean "belt means", and is intended to describe a longitudinal, generally planar member, which may be secured about the waist of a wearer by one or more fasteners. Although embodiments of the invention are defined in terms of a belt having two belt portions, it will be evident that whilst it is possible to provide two belt portions, each one projecting from a respective opposite lateral region of a waist panel, additional belts or belt portions may be provided, as a matter of choice in order to ensure comfort and a secure fit. In addition, the belt may be provided as a single continuous belt with first and second portions projecting laterally from the rear panel of the absorbent article, or as separate belt portions, a first and a second portion of which may be attached to an opposite lateral portion of the rear panel in such a way as to project laterally therefrom. The respective belt portions may be attached to the rear panel by any suitable means. The term: "connection region", should be understood to designate that part of the absorbent article which joins the rear panel to the belt.

Each belt portion has a distal portion which projects laterally away from the connection portion and thereby forms a free end of the respective belt portion. The distal portion comprises the length of the respective belt portion starting from the connection region and ending at a distal end. The distal end encompasses the end edge of the distal portion of the belt portion as well as a distal end region of the said belt portion, the distal end region lying inward of the distal end or distal end edge, and having a dimension, for example between one and five finger widths from the said distal end edge. A connection region between belt portions and the rear panel may be provided on an inside or on an exterior surface of the rear panel. In case a connection region of a belt portion is provided on an interior surface of the rear panel, the belt may wrap around the lateral side edge of the panel to the exterior side where it may be restrained in its retracted position. The wrapping of the belt around the side edge of the rear panel may be arranged such that the belt portion which is wrapped does not protrude beyond the side edge of the rear panel. In this context any amount by which the wrapped portion may appear to project beyond the lateral side edge would not be a useful amount.

Each panel of the absorbent article has an internal and an external surface, the internal surface being the body facing surface. In the same way, the belt or belt portions have an internal or inside surface which, in an extended state of belt, faces a wearer's body. An external or outside surface of the belts or belt portions or body panel or parts thereof is the surface facing away from wearer.

The absorbent article of the disclosure may be configured by a user selectively either in a slip-type configuration, or in a belt-type configuration. In both cases, the front panel may be attached to the belt portions. In order to generate the slip type configuration, the front panel may be brought into engagement with the belt portions in their retracted configuration in which they are held directly or indirectly against the exterior of the rear panel by means of the releasable attachment, in which configuration, the belt portions do not protrude laterally or do not protrude laterally to any significant or useful extent, beyond the side edges of the rear panel. In a belt-type configuration, the front panel may be secured to the belt portions which themselves are in an extended configuration following release of the first releasable attachments and joined about the waist of a wearer. The absorbent article of the disclosure allows a flexible configuration of the article for use, and in particular, allows such flexibility while maintaining comfort and good fit for a wearer. The provision of releasable attachments in association with the exterior side of the rear panel allows the belt portions to be held at least partially on an exterior surface of the article. In this way, there may be prevented a certain bunching of the belt portions on the inside of the article which would occur when worn by a user in a slip type configuration, if the belt portions were, for example, to be stored unrestrained on an interior face of the rear panel.

Furthermore, since belt fasteners are frequently more rigid than belt material, there can be discomfort arising from such fasteners being present on an interior surface of an absorbent article.

In a further embodiment, one or more panel fasteners may be provided in order to secure the front panel to the belt about the waist of a wearer in either an attached condition of the releasable attachments or in a released condition of said releasable attachments. Two configurations thereby generated may respectively correspond to a slip-type configuration or a belt-type configuration.

In a retracted configuration of a belt portion, the distal end region of the belt is releasably attached directly or indirectly to the exterior of the rear panel by means of a releasable attachment. This attachment of the distal end region of the belt to the rear panel includes embodiments in which the distal end region of the belt is attached to a tissue layer overlying a portion of the rear panel, which tissue layer acts as a retainer for the belt portion(s). The retracted form of the belt may be a suitable configuration for packaging and shipping, as well as for use of the article in a slip-type configuration in certain embodiments. Whilst the distal portions of the belt portions are intended to be held directly or indirectly against an exterior surface of the rear panel in retracted positions of the belt portions, according to embodiments of the invention, the connection region between any belt portion and rear panel may nevertheless be located on either an inside or and exterior side of the rear panel with the distal portion being positioned or folded as necessary.

A releasable attachment may be applied to internal or to external surfaces of a belt portion. In this way, the respective belt portions, in a folded condition, may have their distal end region secured to the outside surface of the rear panel. Alternatively, a releasable attachment for holding the belt in a folded configuration may be provided on an inside or outside surface of a belt portion.

The releasable attachments may in particular be provided in the form of one or more releasable bonds between the exterior face of the rear panel and a portion of each of the belt portions which lie parallel to and possibly against the exterior of the rear panel. Alternatively, the releasable attachments may be provided in such a manner that a first belt portion is directly releasably attached to the exterior surface of the rear panel, while a second belt portion overlies the first belt portion and is releasably attached to the outer surface of said first belt portion. The bonds may preferably be provided in the form of adhesive bonds or welds such as ultrasound or hot-melt welds although other possibilities exist. They may be arranged as single location bonds or as multiple bonds. The bonds forming the releasable attachments may be may be spot-bonds. Any releasable attachment may preferably be destroyed upon being released. Alternatively, releasable attachments may be re-attachable. They may be arranged in a pattern, for example in a pattern of spot bonds. Respective releasable attachments may be provided at one or more locations along the length of a respective belt portion. In the aforementioned folded configuration of a belt portion, a fold line is intended to be oriented in a direction generally parallel to the longitudinal axis of the absorbent article such as lie between a first releasable attachment and a second releasable attachment, as seen in a longitudinal direction of each belt portion.

Other suitable materials may be used for the releasable attachment(s) on the belt portion. Such material may include adhesive applied to one or both faces of the belt portion to be attached. Alternatively, the attachment may comprise adhesive tape applied to one or both surfaces, or mechanical fastening means applied to one or both surfaces. For example, the attachment may be comprised of a hook and loop type fastener, or it may be comprised of a mechanical fastening means applied to one surface only, which may attach to a belt portion made from a nonwoven material. It may additionally be any combination of attachments as mentioned herein.

The force needed to separate or release the releasable attachment may preferably be no more than the force which may be readily exerted by the fingers of a user. Nevertheless, in a retracted or folded configuration of the belt portion, in which an attachment is in an attached condition, i.e. intact, the respective attachments should be sufficiently resilient to be capable of withstanding extension forces exerted by a user while putting on the garment, and any forces exerted during normal use, by virtue of being under some tension around a wearer's waist.

In a further embodiment of the invention, the releasable attachment of each belt portion may be provided in the form of a first releasable attachment and a second releasable attachment. In such a case, each second releasable attachment may hold the respective belt portions in a further folded configuration in which a distal end region of each belt portion is releasably secured against another part of that same belt portion. In this way, upon release of the first and second releasable attachments, a secondary extended configuration of respective said belt portions is formed. By this, it is meant that the respective belt portions may be increased in length to a first extended length upon release of the first releasable attachment, and to a second, even greater length, by the release of the second releasable attachment.

When belt portions are provided with first and second releasable attachments, the belt portions may be used for creating the slip-type configuration of the garment, by releasing only the first releasable attachments and without releasing the second releasable attachments at the distal end regions of the respective belt portions. Such a slip configuration may be formed by bringing fasteners, arranged, for example, on the front panel of the absorbent article, which may be arranged at respective opposing lateral regions thereof, into engagement with each one of a first and second belt means in a first extended configuration thereof. Provision of belt means in a folded configuration may allow a greater length of belt to be stored, for example on a rear panel which is relatively narrow.

A belt-type configuration of the product may be created by releasing both the first and second releasable attachments into a secondary extended configuration, and by subsequently joining the respective belt portions by means of the belt fastener about the waist of a wearer, and finally attaching the front panel to the belt thus formed.

The respective waist sizes thereby generated may be substantially equal in both the slip-type and belt-type configurations.

In particular, in order to create substantially equal waist sizes as mentioned, the respective belt lengths and extension lengths may be selected as appropriate. In one embodiment, each belt portion may be extended in length, upon release of a first said releasable attachment, by a length substantially equivalent to at least one half of the length separating two panel fasteners disposed on laterally opposite regions of said front panel, or by a length substantially equivalent to at least one half of the length separating laterally opposite edges of the front panel In a further embodiment, the belt portions comprising the second releasable attachments may be extended in length, upon release of the second attachments, by an aggregate amount substantially equivalent to at least the length separating two panel fasteners disposed on laterally opposite regions of the front panel or by an aggregate amount substantially equivalent to at least the length separating two laterally opposite edges of the front panel An extended or secondary extended configuration of a belt portion indicates a configuration in which the releasable attachment portion of the belt member is released so that the belt member has a length which is greater than the length of the belt member in its folded configuration, i.e. with the attachment in an attached condition. The extended or secondary extended configuration which may be attained by extending the length of the article by means of the first and/or second releasable attachment according to aspects of the invention, is to be distinguished from any increase in length of a belt portion by means of extensible or elastic materials used wholly or partly for the belt or for any of the front or rear panels. Such elastic or extensible materials may be additionally used in embodiments of the present invention.

Embodiments of the invention allow a user, when configuring the article for use, to easily increase the effective length of one or more of the belt portions, prior to joining the belt portions for use, either to each other, or to the front panel. The effective length of the belt portion referred to herein is intended to designate the length of the belt portion measurable between its extremities, in other words, the length extending away from a connection portion of the belt portion towards an extremity created by a fold location—in case the belt portion is in a folded configuration or by a distal end edge—in case the belt is in an extended configuration. Significantly, the capability of increasing the effective belt length which is thereby enabled, allows a user to maintain a constant waist attachment circumference irrespective of whether a slip-type configuration or whether a belt-type configuration is chosen. There is therefore no longer a need to store multiple sizes of article, purely to allow for different attachment methods. In addition, embodiments of the invention allow the length adjustment to be made independently of any extension effects of elastics which may be provided at portions of the belt or at portions of the respective panels.

Advantageously, the length of a belt portion in its folded configuration, measured between the connection region and the extremity of the belt portion, at which the fold line, if the belt is folded, is located (i.e. part-way along the actual extended length of the respective belt portion), may lie in the range between one sixth of the distance between the opposite lateral edges of the front panel, and the full distance between said lateral opposite edges of the front panel (measured in a relaxed laid out flat condition of the panel). Alternatively, the respective length may advantageously lie in the range between one quarter and three-quarters of the distance between the opposite lateral edges of the front panel. As a still further alternative, the respective length may advantageously lie in the range between one third and two-thirds of the distance between the opposite lateral edges of the front panel. As a still further alternative, the respective length may advantageously lie in the range between one quarter and one half of the distance between the opposite lateral edges of the front panel. As a still further alternative, the respective length may advantageously lie in the range between one half and one and one half times the distance between the opposite lateral edges of the front panel. As a still further alternative, the respective length may advantageously be between three-quarters and one and one quarter times the distance between the opposite lateral edges of the front panel.

A folded belt portion having the length discussed in the above paragraph, may be extendable to a secondary extended configuration by releasing the second releasable attachment restraining the folded extremity of the belt portion, to thereby increase the effective length of the belt portion by an amount equal to or greater than one quarter of the distance between the opposite lateral edges of the front panel or by an amount equal to or greater than one quarter of the distance between two fasteners disposed on laterally opposite regions of the front panel. Alternatively, the length of the belt portion in its folded configuration may thereby be increased by an amount equal to or greater than one third of the distance between the opposite lateral edges of the front panel or by an amount equal to or greater than one third of the distance between two fasteners disposed on laterally opposite regions of the front panel. Still further, the length of the belt portion in its folded configuration may thereby be increased by an amount equal to or greater than respectively one half, or two-thirds, or the whole of the distance between the opposite lateral edges of the front panel or by an amount equal to or greater than respectively one half, or two-thirds, or the whole of the distance two fasteners disposed on laterally opposite regions of the front panel. In some embodiments, it may be preferable to provide the extendable length of the folded belt portion of the order of equal to or greater than the distance between the opposite lateral edges of the front panel (or between two fasteners disposed on laterally opposite regions of the front panel), up to one and one half times the said distance. A significant capability to compensate for size discrepancies as a result of different configurations of the article is thereby ensured. Furthermore, the provision of extendable belt means allows for a better fit for individual wearers, because waist dimensions between wearers can vary a great deal, as can, in time, the waist dimensions of an individual wearer.

As can be appreciated, the provision, in certain embodiments of retracted and/or folded belt portions at either side of the rear panel may allow for the front and rear panels to be of reduced width dimensions, because attachment of the front panel may be made by means of fastener means on the front panel being secured on a location on a belt portion. The respective panels need not be made of sufficient dimension to contact each other when worn around the waist of a wearer. In addition, stretchable front panel portions and stretchable panel fasteners further enable the possibility to reduce the width dimensions of the front and rear panels.

The term panel fastener may be interpreted to mean a fastening tab, for example a hook type fastener element combined with a tape section or film or laminate. In order to generate a substantially constant waist size in the two aforementioned configurations, or for increased user comfort, such a fastener tab may be stretchable. A panel section to which a panel fastener is applied may itself include one or more stretchable sections. Thus, in certain embodiments, it may be desirable to provide some extensibility of the front panel by providing stretchable sections of material either as part of the panel fasteners on each lateral side of the front panel, or as part of the lateral side edges of the front panel itself. On the other hand, the panel fasteners may be substantially non-stretchable under loads which may be applied by a user or during use, by a wearer. The amount of the stretchability of a panel fastener or lateral edge region of the front panel may vary depending upon the type of belt which is envisaged and depending upon the dimensions of the front and rear panels. The combined stretchability of the panel fasteners and/or of the lateral edge regions of the front panel, on either lateral side of a front panel, may be such that the total lateral dimension of the front panel, from one edge region thereof, to the other edge region thereof, may be increased by at least one third of the dimension of the front panel as measured when in a relaxed state. More preferably, the front panel may be stretchable to an extent such that the lateral dimension of the front panel may be increased by at least one half or at least two-thirds of the dimension of the front panel in a relaxed state. It is understood that, in most embodiments, at least two panel fasteners are provided on a front panel, whereby each lateral edge region of the front panel is provided with at least one such fastener.

As mentioned above, it is foreseen to use stretchable material particularly in a front panel in order to easily enable a slip-type configuration to be created on a retracted configuration of belt portions. In addition, it may be desirable to provide stretch material in the front panel for purposes of wearer comfort. The amount of stretchable material, and the stretchability of the material will vary depending on the need to enable substantial dimensional increases or upon the need merely to provide for a good, comfortable fit.

Additionally or alternatively, stretchable material may be provided in at least one front or rear panel, for example in a central region thereof, to thereby provide extensibility in a lateral direction of respective said panel. Preferably, the front panel may be stretchable to an extent such that the lateral dimension of the front panel may be increased by at least one quarter or at least one third of the dimension of the front panel in a relaxed state. More preferably, the front panel may be stretchable to an extent such that the lateral dimension of the front panel may be increased by at least one half or at least two-thirds of the dimension of the front panel in a relaxed state. In some cases it may be desirable for the panel fasteners to be substantially non-stretchable, in particular, where sufficient stretchability is provided in one or both of the front and rear panels.

Stretchable material segments provided for allowing substantial extension of the dimension of the front panel, including the lateral edge regions thereof should preferably be extensible to 10% elongation under a force of between 45-250 g/25 mm as measured by test ASTM D-882. Preferably, the force required lies between 55-210 g/25 mm, still preferably between 65-180 g/25 mm, still preferably between 75-150 g/25 mm, still preferably between 80-120 g/25 mm, still preferably between 84-105 g/25 mm, still preferably between 88-98 g/25 mm. Alternative possible ranges include values between 85-150 g/25 mm, or between 65-100 g/25 mm.

Advantageously, the material employed may exhibit a force at 100% elongation, as measured by test method ASTM D-882 of between 200-550 g/25 mm. Preferably, the said force required for 100% elongation lies between 230-470 g/25 mm, still preferably between 250-400 g/25 mm, still preferably between 260-450 g/25 mm, still preferably between 270-400 g/25 mm, still preferably between 280-350 g/25 mm, still preferably between 290-330 g/25 mm or 300-340 g/25 mm. Alternative possible ranges include values between 280-550 g/25 mm, or between 200-360 g/25 mm. The same materials may be used for providing stretchability in the form of elasticity in the belt portions, in which the same stretch force parameters may be applied.

Fasteners, in the form of panel fasteners may be attached to the front panel for attaching the front panel to either the belt connected around the waist of a wearer, or to the respective first and second (or more) belt portions drawn partially about the wearer. To this end, fasteners may be provided on the front panel at various places on the panel as may be necessary. Preferably, the panel fasteners are arranged such that at least one fastener is located on the front panel at or near each opposite lateral region of said panel, preferably on an inside surface of the front panel. In some cases it may be desirable to place fasteners on an outside surface of the front panel. In this way, the attachment of the front panel, including its lateral edges, to the belt portions is ensured, irrespective of the configuration selected by a wearer or user. Alternatively, a fastener may be provided in the form of a strip across substantially all of the front panel.

The fasteners may be releasable and may comprise any suitable alternatives known in the art. For example, adhesive tape sections or tabs, possibly covered by a release layer may be envisaged, as well as mechanical fastening means such as hook and loop tape fastenings or hook type fastenings which may engage with fibres of a belt material, such as a nonwoven material. Still further, panel fasteners may be provided as hook type means co-operating with loop-type material sections provided upon the belt portions.

In the foregoing, it should be noted that the article is intended to be reversible. That is to say, that the article may be placed on a wearer with the rear panel, from which the belt portions project outwardly, at the front of the body of said wearer, with the belt members then extending rearwardly, either wholly or partially about the waist of the wearer, in either a folded or extended configuration, to be closed in either a belt-type or slip-type configuration. Typically, users may prefer to configure a slip-type configuration of the article with the front panel placed at the rear of the body and the rear panel at the front of the body, with the belt portions extending rearwardly about the waist of the wearer. In this way, the forces needed to be exerted, in fastening lateral portions of the front panel to the belt portions, may be exerted by the arms of the wearer grasping the lateral edge region of the front panel and pushing in a forwards direction to place it over the corresponding belt portion and to thereby secure it in place. A user placing the article in the belt-type configuration may prefer to place the rear panel to the rear of the body, releasing an attachment of a belt portion and drawing the free ends of the respective belts in a forward direction about the waist before joining them together around the front of the body by means of a fastener. Also in this case, forces needed to be exerted in drawing the belt portions around the waist of a wearer may be exerted by a pushing action of the arms in a forward direction.

BRIEF DESCRIPTION OF THE DRAWINGS

The disclosure will be better understood by reference to the accompanying drawings. The drawings are intended to show examples of ways of carrying out embodiments of the invention. The examples are for illustrative purposes and are not intended to limit or suggest any limitation to the scope of the disclosure.

FIG. 8c illustrates a particular embodiment for restraining the belt portions in a retracted configuration.

DETAILED DESCRIPTION OF THE PREFERRED EMBODIMENTS

Figure 1:
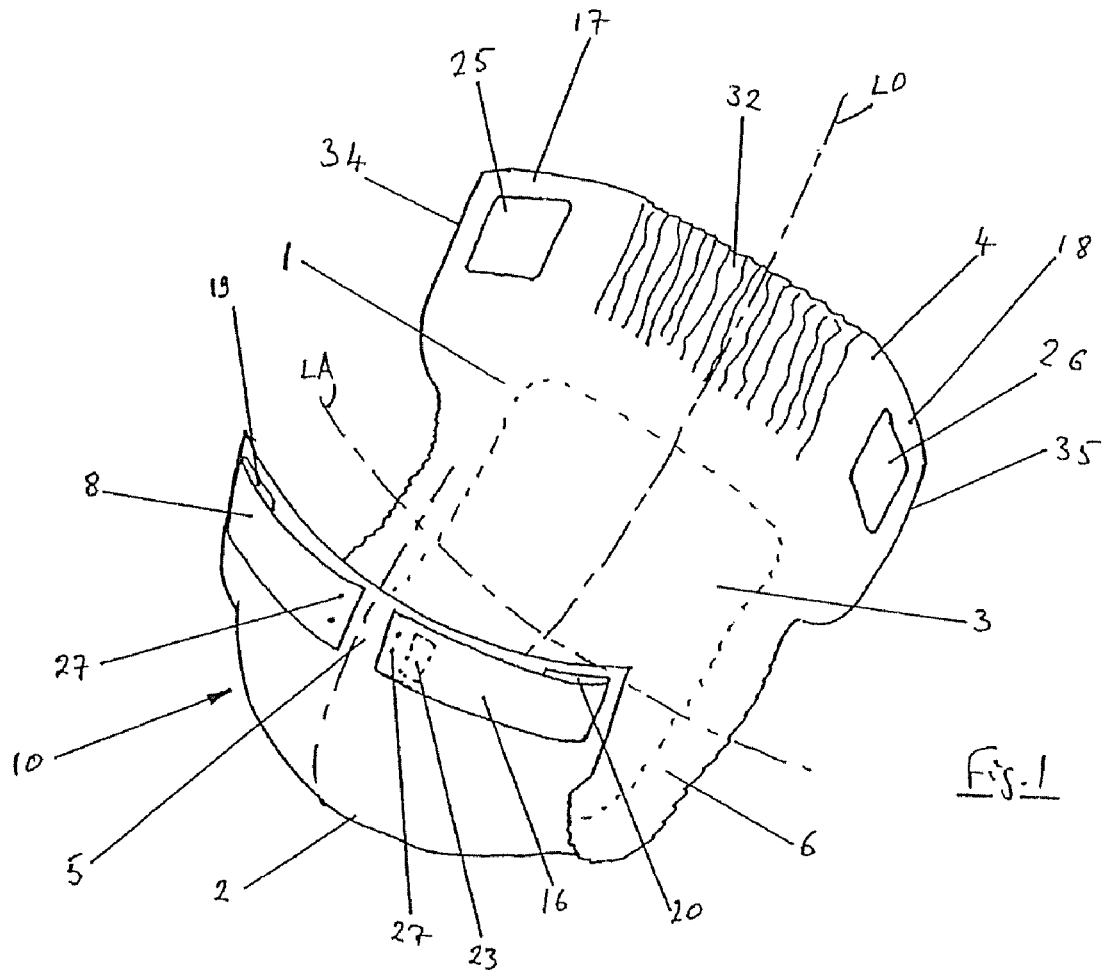
FIG. 1 shows a perspective schematic view of an article according to the disclosure with both belt portions in a retracted position.

A general illustration of a possible construction of an article according to the disclosure is illustrated in FIG. 1. The absorbent article illustrated shows a body panel 10 (or chassis), which is comprised generally of a crotch region 6, between a front and a rear panel, denoted respectively as 4 and 5. The illustrated body panel 10 has lateral side edges 34, 35 extending from the rear panel to the front panel. The article has an outer impermeable layer in the form of a backsheet 2, illustrated at the outer surface of the article. A topsheet 1 is provided on the inside upper surface of the article. An absorbent core 3 lies between the topsheet 1 and the backsheet 2. Many other layers may be provided. Each layer may be unitary or composite. For example, an absorbent core 3 may be made from predominantly a single material, or from a combination of materials provided as laminates or distributed in respective areas of the absorbent core. Many different kinds of absorbents, backsheets 2, and topsheets 1 as well as other layers are known in the art for the purpose of their use in absorbent articles. The terms front panel and rear panel are used for the purpose of defining parts of the article in relation to each other, and may, in use, freely be placed on a wearer in a position in which the front panel is to the rear of the body of a wearer, while the rear panel is placed to the front body portion of a wearer. To this end, the absorbent core 3 may, in some embodiments, be symmetrical about a lateral centreline (not shown) of the article. The crotch portion 6 and the respective panels 4, 5 may be integral or made from separate elements. A longitudinal axis LO in a lengthwise direction of the article and a transverse axis LA in a lateral direction of the article are indicated for reference purposes. As can readily be seen, the article as illustrated defines a generally interior surface which is intended to lie against the body of a wearer, and an exterior surface intended to face outwardly of the body when the article is in place on a wearer.

A belt is comprised of two belt portions, a first belt portion 8 and a second belt portion 16, although both belt portions could be made from a single piece. The belt portions 8 and 16 are shown attached to the rear panel 5 at connection portions 19, 20. They may be made of any suitable material, such as a film type or fibrous material. An example of a fibrous material may be a nonwoven fibrous material made from polyethylene or polypropylene fibres. Some other suitable materials for a belt of the present disclosure, as well as a method for making same are disclosed for example in WO 03/017904. Composite materials and combinations of materials for the belts may also be envisaged, such as laminar materials. A variety of nonwoven materials for use in the belt portions may be used. Examples of materials include a composite material made from a laminate of a carrier material which forms the outside of the belt and a soft nonwoven which forms the inside of the belt, intended to bear directly on the user's skin. A suitable nonwoven material can consist of a spunbond material, for example of polypropylene or polyethylene fibres. Bi-component fibres can also be used. Another suitable nonwoven material consists of a carded heat-bonded material, for example polypropylene, polyester or bi-component fibres. As the carrier material it is possible to use a plastic film or other suitable material, for example the aforementioned nonwoven materials. The carrier material can be adapted to function as a receiving surface for front panel fastening devices shown as panel fasteners 25, 26 in FIG. 1. In the case where these consist of adhesive tapes, a plastic film may be suitable and may co-operate with a corresponding landing zone (not shown) on each of the belt portions 8, 16. In the case where other types of fastening devices are used instead of adhesive tapes, for example hook and loop materials, another type of carrier material is needed which can function as a receiving surface for the fastening device in question. An important detail is that the belt parts 8, 16 are preferably breathable so as not to occlude the skin of the user wearing them. In order to provide a comfortable fit, the width of the belt parts 8, 16 may be between 5 and 20 cm, preferably between 7 and 15 cm.

Figure 8:
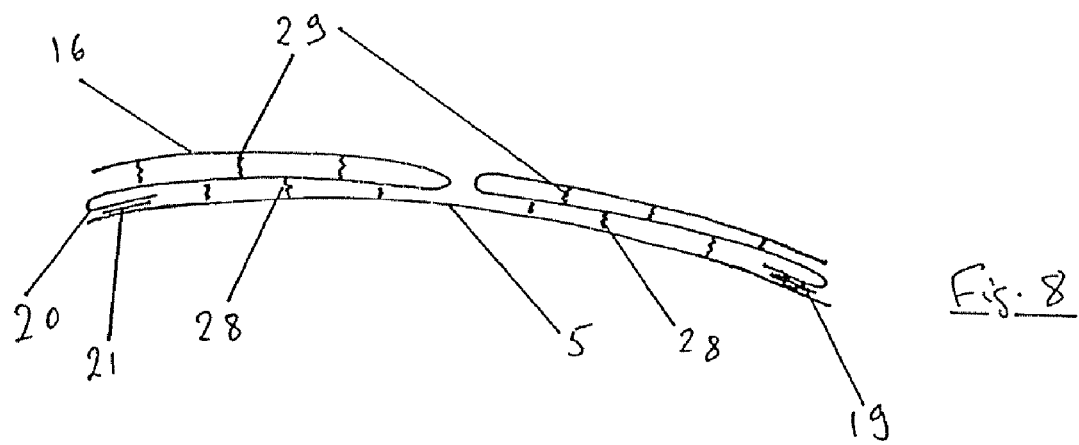
FIG. 8 illustrates in detail a possible folded belt configuration having first and second releasable attachments.
Figure 8A:
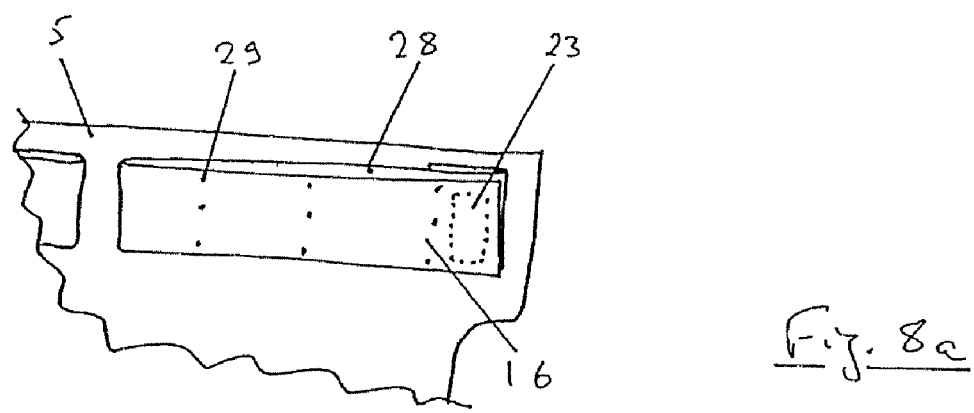
FIGS. 8a and 8b illustrate alternative possibilities for configuring the releasable attachments on the belt portions.
Figure 8B:
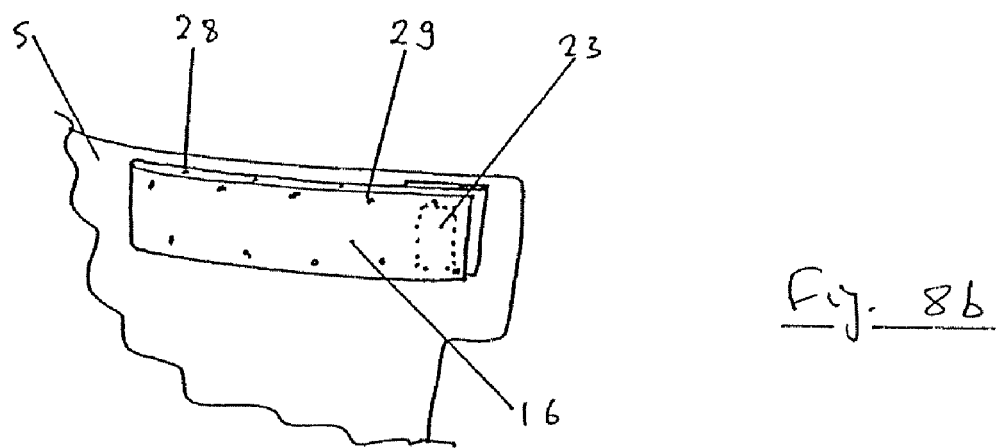

The connection portions 19, 20 are located at laterally opposite side regions of the rear panel, inwardly of the respective opposite lateral side edges 34, 35 of the rear panel 5. In FIG. 1, the connection portions 19 and 20 are shown extending from the inmost extent of one end of the first and second belt portions 8, 16, outwardly towards the respective opposite lateral edges 34, 35 of the rear panel 5. Connection between the belt portions 8, 16 and the rear panel 5 may be by any suitable means 21 (FIG. 8) such as adhesive means or weld or hot melt means. In certain embodiments (not illustrated), the belt portions 8, 16 may be made from the same material as the material from which the rear panel 5 is made, in such cases, there may be no side edges of the rear panel 5 as such. Respective oppositely arranged lateral edge regions of the front panel 4 are indicated by numerals 17 and 18.

Figure 3:
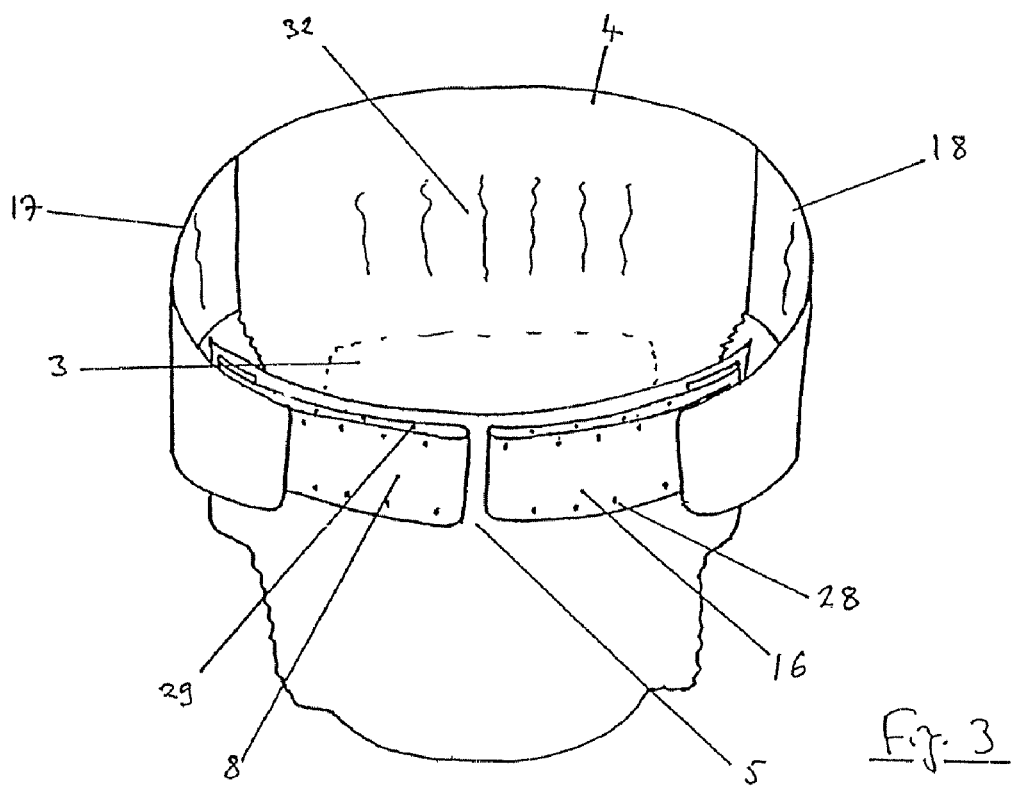
FIG. 3 shows a schematic view of an article according to FIG. 2 in a slip-type configuration with both belt portions retracted.

In FIG. 1, the belt portions 8, 16 are shown in a retracted extended state, suitable for storage and shipping and suitable for configuration into a slip-type construction of the absorbent article as illustrated by way of general example in FIG. 3. Such a configuration may be made up by drawing the lateral edge regions 17, 18 including panel fasteners 25, 26 about the waist of a wearer and attaching the fasteners 25, 26 to a respective belt portion 8, 16.

In FIG. 1, the belt portions 8 and 16 are each held in a retracted configuration against the outside surface of the rear panel 5 by means of a releasable attachment 27. In the case illustrated in FIG. 1, two spot bonds or welds or adhesive spots are used as a releasable fastener. In some embodiments such releasable attachment means 27 may comprise single or multiple spot bonds or welds or adhesive spots.

Figure 1A:
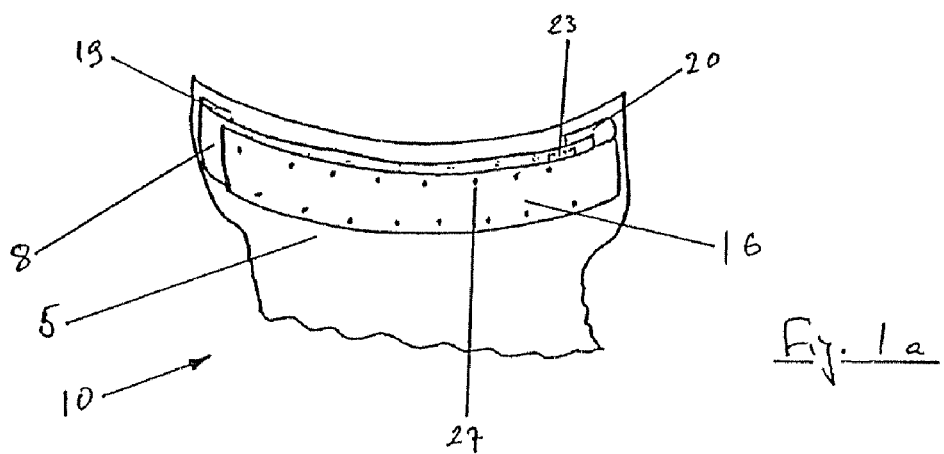
FIG. 1a illustrates an alternative way of securing the belt portions in a retracted configuration

In FIG. 1a, a variant is illustrated according to which a first and a second belt portion 8, 16 are provided with a releasable attachment 27 in the form of bonds releasably joining the two belt portions 8, 16 together in a retracted configuration in which they overlap at the exterior surface of the rear panel. In addition, the first belt portion 8 may optionally be releasably attached to the outer surface of the rear panel 5.

A belt fastener 23 is indicated generally in FIGS. 1 and 1a. The belt fastener 23 may be placed on an inside or outside surface of a belt portion 8, 16.

The article may be deployed in a belt-type configuration for use by a wearer by releasing the releasable attachment 27 and attaching the belt fastener 23, provided, as shown by way of example, at a distal end region of the second belt portion 16, to the first belt portion 8. The first belt portion 8 may in turn be provided with one or more landing zones for the belt fastener 23. Alternatively, the fastener may be attachable anywhere along the length of the first belt portion 8. In one embodiment, the fastener 23 may comprise a mechanical fastening means, such as barb-type or hook-type tab, while the belt portions 8, 16 may be made from a fibrous material with which the mechanical fastener may become engaged.

Figure 4:
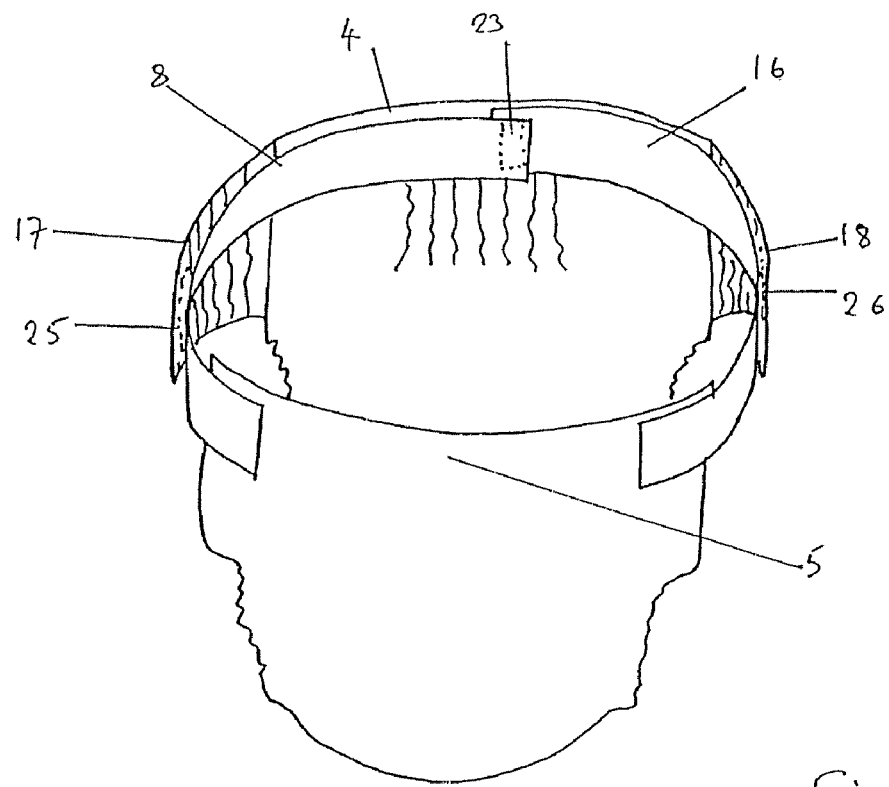
FIG. 4 shows a schematic view of an article according to FIG. 2 in a belt-type configuration.

Alternatively, the fastener 23 may be an adhesive element, which may be covered by a release tape. Such an adhesive element may be attachable anywhere along the length of a belt portion 8, 16 and it may co-operate with landing zones provided at one or more locations along a belt portion 8 or 16. Another possible fastener may comprise a tab with a hook-type connection portion and also having an extensible or elastic portion. An example of a belt-type configuration of one embodiment of the present disclosure is shown at FIG. 4.

Stretchability of the article may be provided by providing panel fasteners 25, 26 as elastic hook tabs (not shown), or by providing an elastic portion 32 in the front panel 4. As an alternative (not shown) the belt portions 8 and 16 may be provided either wholly or partially from stretchable material.

Figure 2:
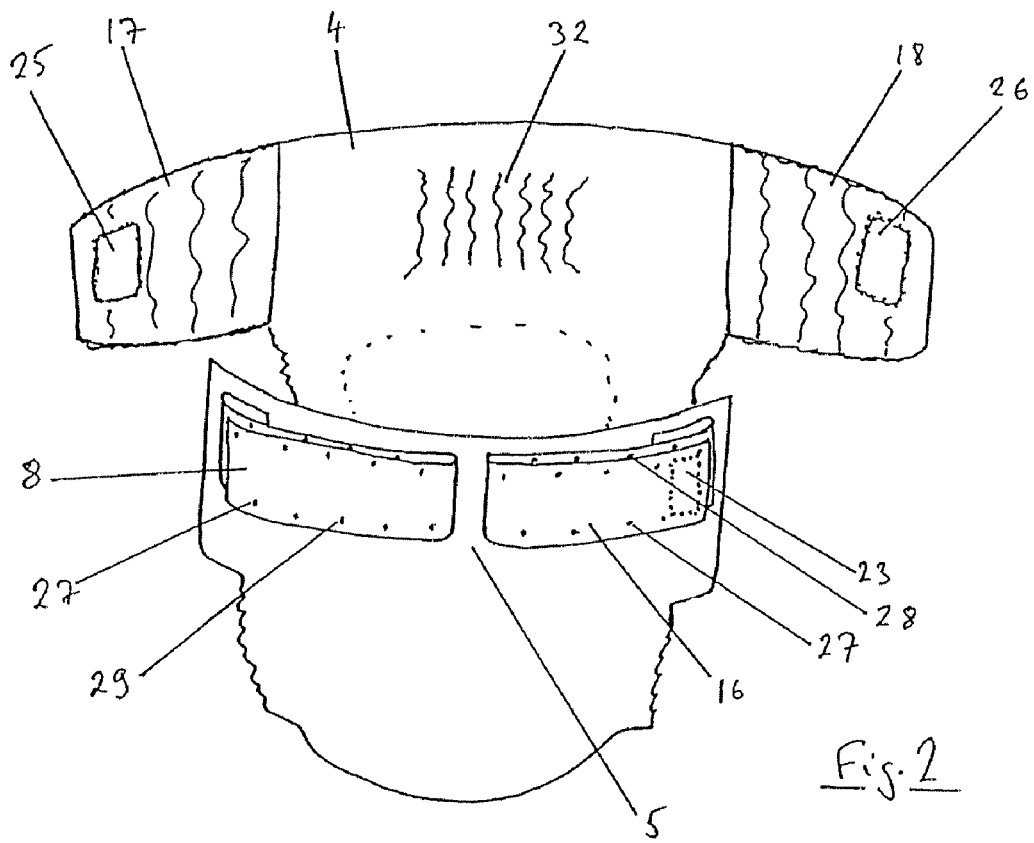
FIG. 2 shows a perspective schematic view of an article according to other aspects of the disclosure with both belt portions in a retracted position and having stretchable means at various places on the front panel.
Figure 5:
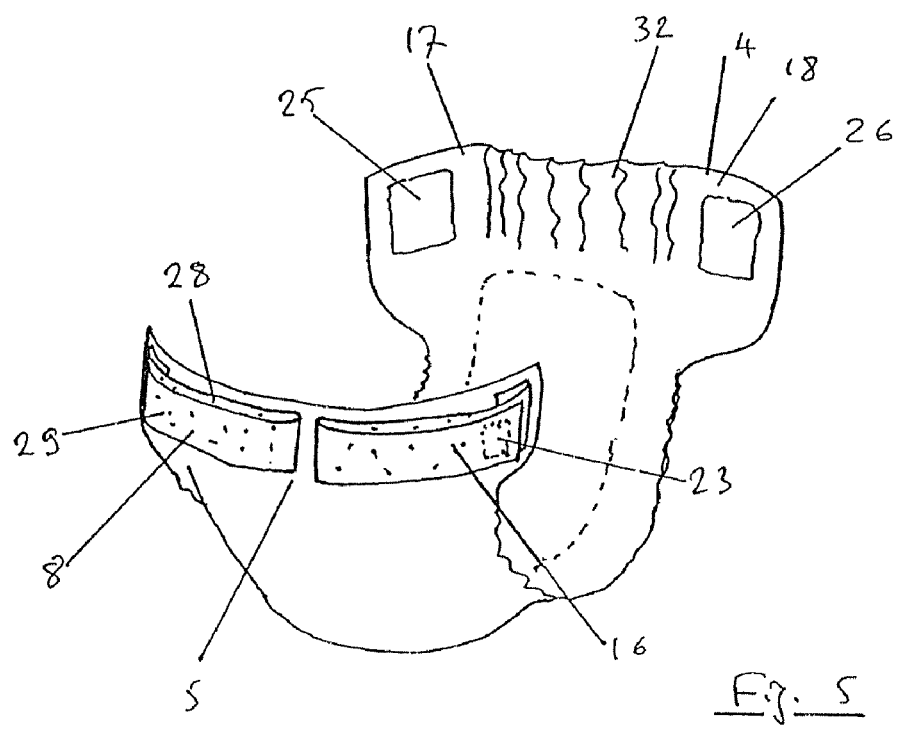
FIG. 5 shows a perspective schematic view of an article according to other aspects of the disclosure with both belt portions in a retracted and folded position.

FIG. 2 shows a further embodiment of the present disclosure, in which substantial stretchability of the article may be provided by including elastic materials in the respective lateral edge regions 17 and 18 as well as, optionally an elastic portion 32 in a central region of the front panel 4. Belt portions 8, 16 are provided in a folded retracted configuration, from which they may be extended into a first and a secondary extended configuration. To this end, releasable attachment means 27 may be provided on each belt portion 8, 16 as a first releasable attachment 28 and a second releasable attachment 29. The illustrated article thereby has a great degree of flexibility in terms of the ways in which it may be deployed for use. On the one hand, the stretchability of the elastic material portions 32 and 17 and 18 may allow for the article to be drawn out to the required dimensions to reach about the waist of a user for fastening the fasteners 25, 26 directly to the retracted belt portions 8, 16, in an attached condition of both the first and the second releasable attachments 28, 29. Such a configuration is shown in FIG. 3 and corresponds to a slip-type configuration. Alternatively, the belt portions 8, 16 may be deployed by releasing the respective first releasable attachments 28 only, to thereby form a slip type configuration about a wearer (see e.g. FIG. 6) in which a lesser degree of stretchability of the front panel and lateral edge regions is required than that needed for the configuration shown in FIG. 3. FIG. 5 illustrates an example of an embodiment of the disclosure in which stretchability of the front panel is provided by means of an elastic or creped portion in a central region of the front panel 4 only. Additional stretchability may be attained by combining the stretchable central portion with stretchable portions in other parts of the front panel 4 or the belt portions 8, 16. Alternatively, additional stretchable portions such as illustrated in FIG. 2 or a continuous stretchable portion extending across substantially the entire width of the front panel may be provided as illustrated in FIG. 7.

Figure 7:
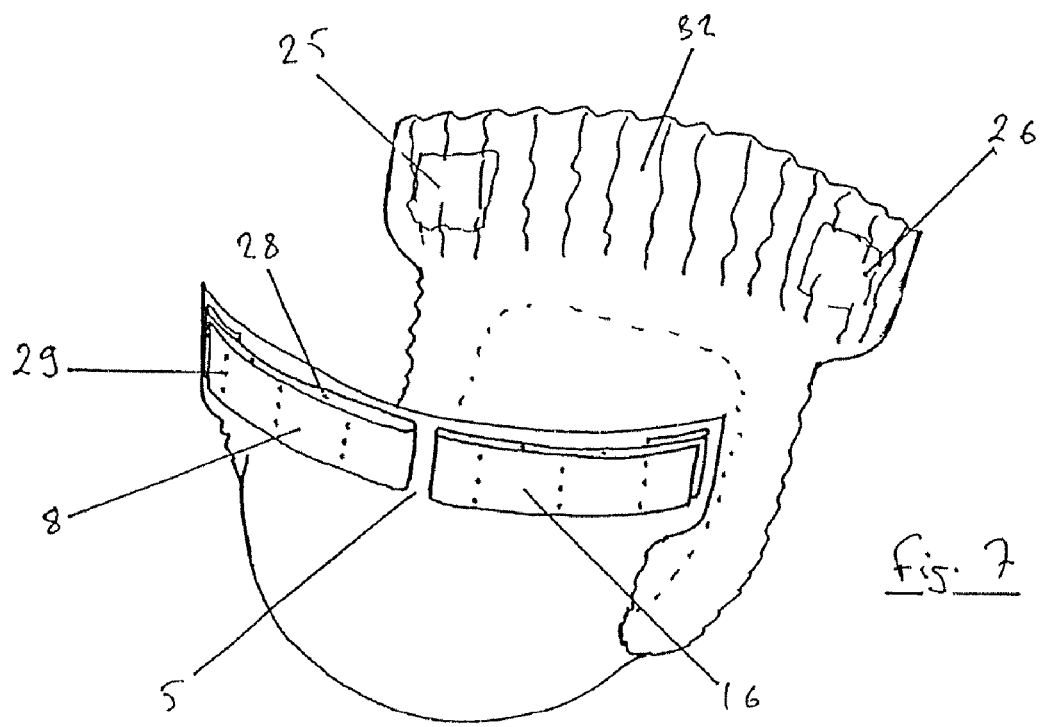
FIG. 7 shows a schematic view of an embodiment of the article having a fully stretchable front panel portion.

In FIG. 7, a material which is capable of some plastic deformation at low levels of force may be used in the backsheet layer in order to accommodate for substantial extension of the stretchable portion 32 of the front panel which extends across substantially the full width of the panel.

As a still further alternative, the article may be deployed in a belt-type configuration by releasing both the first and second releasable attachments 28, 29 to fully extend the belt portion into a secondary extended configuration, thereby allowing the belt to be fastened about the waist of a wearer by means of belt fastener 23, as shown in FIG. 4.

As can be seen from various embodiments illustrated, an absorbent article according to the disclosure, may in particular be provided with two belt portions 8, 16. The belt portions 8 and 16 may, in the form in which they are illustrated, be employed for the configuration of the absorbent article into a slip-type configuration for wearing, wherein the front panel 4, may be placed at the rear of a wearer's waist, with the fasteners 25, 26 provided by way of example at lateral edge regions 17, 18 of the panel 4, and on an internal surface thereof, being brought forwards about the wearer and secured against a corresponding belt portion 8, 16. One or more fasteners 25, and 26 may additionally or alternatively be provided on the external surface of the panel 4 (not shown). Alternatively, fasteners 25, 26 may be provided at the lateral edges of the front panel as adhesive fastener tabs which may be peeled off from a release layer on the front panel and attached to an appropriate portion on the belt. The belt portions 8, 16 may be made from a material to which a fastener 25, 26 may be readily attached. To this end, one or more fasteners may be made of an adhesive strip or mechanical fastening means such as a hook type fastener capable of securely engaging with either a fibrous material of the belt portions 8, 16. For certain types of fasteners, appropriate landings (not shown) may be provided on belt portions 8, 16 for receiving adhesive or mechanical fasteners 25, 26. In other embodiments, additional fasteners 25, 26 may be provided (not shown), or the fasteners may be provided as a single fastener (not shown) covering a larger portion of the width of the front panel.

Releasable attachment 27 or 28 or 29 may, according to various embodiments, extend along a length of the belt portion 8. The extent of the attachment 27, 28, 29 is thereby more than local, although the attachment is releasable in the same way as the attachment 27 illustrated in FIG. 1, namely by applying finger force of a user in a manner to separate the two layers. In particular, by grasping a free distal end of the belt portion 8 nearby the distal edge and pulling in a direction to separate the layers. The releasable attachment 27, 28, 29 may be provided as a weld or adhesive line, although other possibilities for creating the attachment 27 exist, as already discussed. Examples of releasable attachments are additionally shown in FIGS. 8 and 8*a*-8*c*. As can be seen, for ease of detachment, the releasable attachment 27 may be provided in the form of discrete bonding points at staggered locations along the folded belt portion. The staggered locations may each comprise lines of individual bond points or they may be comprised of a zig-zag pattern of bond points. The bonds may be of any suitable type and may include adhesive spots or spot welds.

In certain embodiments, a releasable attachment may be provided on the rear panel 5 in the form of a retainer 39 made from a piece of tissue (FIG. 8*c*) underlying or overlying at least the distal end regions of respective belt portions 8, 16, to thereby hold these in place against the rear panel 5. The tissue layer for the retainer 39 may be of any suitable material, in particular, it may be a fibrous layer or a nonwoven layer. In some cases, the tissue layer may be attached to the rear panel 5 only, with the belt ends underlying the retainer 39. The retainer 39 or tissue layer may be attached to the rear panel 5 by means of spot welds or adhesive spots. The retainer 39 may also be attached directly to each belt portion. The belt may be deployed by destroying the retainer 39 and releasing the respective belt portions 8, 16. To that end, lines of weakness 37 may be provided in the tissue layer 39, which are designed to allow release of the belt portions 8, 16 from their restrained (folded) configuration. Second releasable attachment means 28 may be provided additionally to the retainer means 39 in cases where a first and a second degree of extension of the belt is desired, or when a larger extensibility of the belt is required than can be achieved with a single releasable attachment.

Owing to the various possibilities for increasing the length of the belt portions 8, 16 and the front and rear panels 4, 5, the circumference of the article about the waist of the wearer in the belt-type configuration, may therefore be substantially equal to the circumference of the article about the waist of the wearer in the slip-type configuration.

Some stretchability of belt portions or parts thereof, or of the front panel 4 may be provided by including elastic means or by means of pleating. Combinations of pleated or creped portions (not shown) and elastic portions 32 may also be used.

A wide range of materials may be employed for providing stretchability. Such elastic materials may comprise an elastomeric material that exhibits elastomeric properties at ambient conditions, i.e., the material will substantially resume its original shape after being stretched. Preferably, the elastic material will sustain only a small permanent set following deformation and relaxation, which set is preferably less than 30% and more preferably less than 20% of the original 50% to 500% stretch. The elastomeric material can comprise either one or more pure elastomers or blends with an elastomeric phase or content that will still exhibit substantial elastomeric properties at room temperature. Suitable elastomeric thermoplastic polymers include block copolymers or the like. These block copolymers are described in, for example, U.S. Pat. Nos. 3,265,765; 3,562,356; 3,700,633; 4,116,917 and 4,156,673. Particularly useful are styrene/isoprene, styrene/butadiene or ethylenebutylene/styrene block copolymers. These blocks may be arranged in any order including linear, radial, branched or star block copolymers. Other useful elastomeric polymers can include elastomeric polyurethanes, elastomeric ethylene copolymers such as ethylene vinyl acetates, ethylene/propylene copolymer elastomers or ethylene/propylene/ diene terpolymer elastomers. Blends of these elastomers with each other or with modifying elastomers are also contemplated. Elastic laminates are also suitable for use as material in the belt parts 8, 16. Such laminates can have one or two or more nonwoven layers which may be attached to an elastic material layer, preferably between at least two nonwoven layers. In case only a single nonwoven layer is used in such a laminate, then it is preferable that the nonwoven layer should face towards the wearer when the article is configured for use in order to increase wearer comfort. The elastic layer can be chosen from threads, adhesives or films. Preferred elastomeric materials for an elastic layer are olefinic elastomers, e.g. ethylene-propylene elastomers, ethylene propylene diene polymer elastomers, metallocene polyolefin elastomers or ethylene vinyl acetate elastomers, or styrene/isoprene, butadiene or ethylene-butylene/styrene (SIS, SBS, SEBS) block copolymers, or polyurethanes or blends. In addition, all elastomeric materials having an elasticity between 10-500% may be useful for embodiments of the present disclosure.

As already mentioned, the releasable attachments 28, 29 or 27 of any of the embodiments of the disclosure may be destructible (non re-fastenable) upon separation, or they may be refastenable to extend either or both belt portions 8, 16 to a length intermediate a full extended length and a folded length. In either case, when the belt portions are restrained in a folded configuration, they need to be restrained at least to an extent such that they withstand a pulling separating force which might arise, for example during shipping. On the other hand, they should be sufficiently loosely restrained so that they can easily be detached by a user without causing damage to the article or to the belt portions themselves. To this end, any fastening members or means which comprise the releasable attachment 28, 29 or 27, should be designed to be releasable under a force between about 3-15N. It has been found that bonds or joins used for the releasable attachments should have a separating strength exhibiting a minimum resistance of 3N, in order to maintain product integrity during shipping and handling, whilst user comfort and prevention of damage to the article is best ensured when forces below 15N are needed for product deployment. These forces are intended to apply to an absolute pulling force applied to a 25 mm wide belt length in the plane of the product in a direction such as to separate two members, i.e. at a 180° angle to the bond or join location. Still preferably, the releasable attachments exhibit separating forces between 4-ION, and still preferably between 5-7N. A force of 5-6N or of approximately 5N or approximately 6N may be preferred. The bond strength may vary for belts which are wider or narrower than 25 mm. In particular, the relationship between a variation in width and a variation in 25 the bond strength should be linear, percentage-wise relative to the strength values given for the 25 mm example belt width and the force values given above. In other words, an approximately ten percent higher required separating force of the releasable fastener may suitably be applied for an approximately ten percent increase in the belt width. A test method to be employed for measuring the above 30 delaminating separating forces may be according to ASTM D 1876-72.

Figure 6:
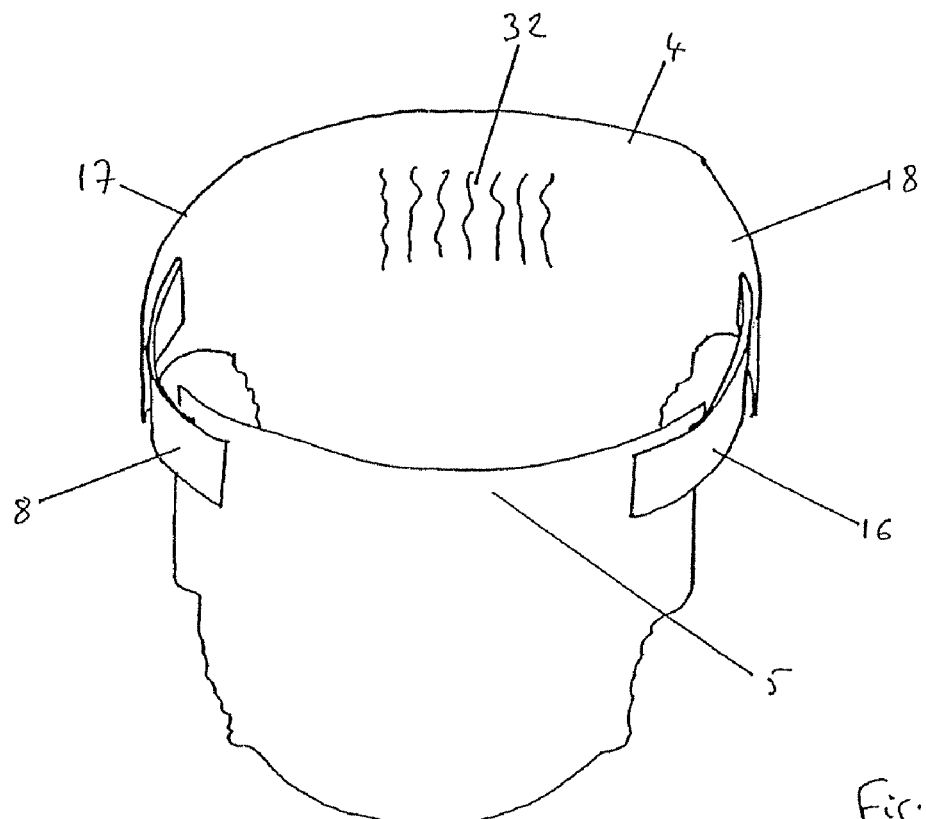
FIG. 6 shows a schematic view of an article according to FIG. 5 in a slip-type configuration.

FIGS. 6 and 3 show an illustration of the garment in a slip-type configuration, in which the front panel may be placed at the rear of a user. The connection between the belt portions 8, 16 and the front panel 4 may be made by any suitable means as an alternative to the panel fasteners 25, 26 illustrated. In particular, fasteners could be provided on the belt portions 8, 16 themselves, or on both belt portions and front panel 4.

Variants of the above examples, which are not shown, may be provided without departing from the scope of the present invention. In particular, the article may be provided with a range of attachment means or fasteners for fulfilling the constructions and functions as per the appended claims.

The invention claimed is:

1. An absorbent article having a topsheet, a backsheet and an absorbent core therebetween;
   said absorbent article comprising a body panel having a longitudinal axis extending in a longitudinal direction and a transverse axis extending in a lateral direction, said body panel further comprising a crotch region between a front panel and a rear panel, said crotch region and said front and rear panels each having an interior face and an exterior face;
   said absorbent article comprising a belt comprising a first belt portion and a second belt portion;
   said first and second belt portions each having a distal portion extending laterally from a respective connection region, at which connection region, said belt portion is joined to said rear panel by an initial attachment;
   said absorbent article further comprising a belt fastener near a distal end of at least one of said belt portions which fastener is capable of securing said first and second belt portions to each other about the waist of a wearer;
   wherein said absorbent article further comprises a releasable attachment in association with each respective said first and said second belt portion which, when in an attached condition, secures said belt portions in a retracted configuration, in which retracted configuration the distal end of each said belt portion does not extend beyond a longitudinally extended end of the respective connection region, and in which retracted configuration a distal end region of each said belt portion is releasably restrained directly or indirectly against said exterior face of said rear panel and whereby upon release of said releasable attachment, an extended configuration of respective said belt portion is formed, in which extended configuration, said belt portions may be joined to one-another by said belt fastener, wherein said absorbent article further comprises one or more panel fasteners which enable securing said front panel with said belt, and wherein said absorbent article is configured such that it may be secured and worn about the waist of a wearer in both an attached condition of said releasable attachments and in a released condition of said releasable attachments.

2. The absorbent article according to claim 1, wherein stretchable material is provided in at least one front or rear panel to thereby provide extensibility in a lateral direction of respective said panel.

3. The absorbent article according to claim 1, wherein when said front panel is attached to said respective belt portions in said retracted configuration of said belt portions, a substantially same waist size of said absorbent article may be generated as in when said front panel is attached to said belt portions in an extended configuration thereof, when they are joined to one-another by said belt fastener.

4. An absorbent article having a topsheet, a backsheet and an absorbent core therebetween;

said absorbent article comprising a body panel having a longitudinal axis extending in a longitudinal direction and a transverse axis extending in a lateral direction, said body panel further comprising a crotch region between a front panel and a rear panel, said crotch region and said front and rear panels each having an interior face and an exterior face;

said absorbent article comprising a belt comprising a first belt portion and a second belt portion;

said first and second belt portions each having a distal portion extending laterally from a respective connection region, at which connection region, said belt portion is joined to said rear panel by an initial attachment;

said absorbent article further comprising a belt fastener near a distal end of at least one of said belt portions which fastener is capable of securing said first and second belt portions to each other about the waist of a wearer;

wherein said absorbent article further comprises a releasable attachment in association with each respective said first and said second belt portion which, when in an attached condition, secures said belt portions in a retracted configuration, in which retracted configuration a distal region of each said belt portion is releasably restrained directly or indirectly against said exterior face of said rear panel and whereby upon release of said releasable attachment, an extended configuration of respective said belt portion is formed, in which extended configuration, said belt portions may be joined to one-another by said belt fastener, wherein said absorbent article further comprises one or more panel fasteners which enable securing said front panel with said belt, wherein said absorbent article is configured such that it may be secured and worn about the waist of a wearer in both an attached condition of said releasable attachments and in a released condition of said releasable attachments, and wherein each said releasable attachment is comprised of a first and a second releasable attachment in association with each said first and said second belt portion, wherein said first releasable attachment serves to hold a said respective belt portion in a retracted position against said rear panel, while said second releasable attachment holds a respective said belt portion in a folded configuration in which a distal end region of each said belt portion is releasably secured against another part of the same said belt portion, wherein upon release of said second releasable attachments and said first releasable attachments, a secondary extended configuration of respective said belt portions is formed, and wherein the first and second releasable attachments are different from the initial attachment.

5. The absorbent article according to claim 4, wherein the one or more panel fasteners are capable of securing said front panel with said belt about the waist of a wearer in both a first extended configuration of said belt portions in which only said first releasable attachments are released, and in the secondary extended configuration of said belt portions, in which both first and second releasable attachments are released, and wherein, when said front panel is attached to said respective belt portions in said first extended configuration of said belt portions, a substantially same waist size of said absorbent article may be generated as in when said front panel is attached to said belt portions in said secondary extended configuration of said belt portions when they are joined to one-another by said belt fastener.

6. The absorbent article according to claim 1, wherein said one or more panel fasteners are arranged such that at least one fastener is located on said front panel at or near each opposite lateral region of said panel.

7. The absorbent article according to claim 1, wherein stretchable material is provided in said front panel such that the lateral width dimension of said front panel may be increased by at least one third upon extension of the front panel in the lateral direction.

8. The absorbent article according to claim 1, wherein said belt portions are made from nonwoven material capable of being securely engaged by a mechanical or adhesive belt fastener or panel fastener.

9. The absorbent article according to claim 4, wherein each said belt portion may be extended in length, upon release of the first said releasable attachment, by a length substantially equivalent to at least one half of the length separating two panel fasteners disposed on laterally opposite regions of said front panel.

10. The absorbent article according to claim 4, wherein each said belt portion may be extended in length, upon release of a first said releasable attachment, by a length substantially equivalent to at least one half of the length separating laterally opposite edges of said front panel.

11. The absorbent article according to claim 4, wherein said belt portions comprising said second releasable attachments, may be extended in length, upon release of said second attachments, by an aggregate amount substantially equivalent to at least the length separating two panel fasteners disposed on laterally opposite regions of said front panel.

12. The absorbent article according to claim 4, wherein said belt portions comprising said second releasable attachments, may be extended in length, upon release of said second attachments, by an aggregate amount substantially equivalent to at least the length separating two laterally opposite edges of said front panel.

13. The absorbent article according to claim 4, wherein said first and/or said second releasable attachments are destroyed upon separation thereof.

14. The absorbent article according to claim 1, wherein in said retracted configuration, at least a portion of said first and second belt portions is releasably restrained directly against said exterior face of said rear panel at a location different from said connection regions.

15. An absorbent article having a topsheet, a backsheet and an absorbent core therebetween;

said absorbent article comprising a body panel having a longitudinal axis extending in a longitudinal direction and a transverse axis extending in a lateral direction, said body panel further comprising a crotch region between a front panel and a rear panel, said crotch region and said front and rear panels each having an interior face and an exterior face;

said absorbent article comprising a belt comprising a first belt portion and a second belt portion;

said first and second belt portions each having a distal portion extending laterally from a respective connection region, at which connection region, said belt portion is joined to said rear panel by an initial attachment;

said absorbent article further comprising a belt fastener near a distal end of at least one of said belt portions which fastener is capable of securing said first and second belt portions to each other about the waist of a wearer;

wherein said absorbent article further comprises a releasable attachment in association with each respective said first and said second belt portion which, when in an attached condition, secures said belt portions in a retracted configuration, in which retracted configuration a distal region of each said belt portion is releasably restrained directly against said exterior face of said rear panel and whereby upon release of said releasable attachment, an extended configuration of respective said belt portion is formed, in which extended configuration, said belt portions may be joined to one-another by said belt fastener, wherein said absorbent article further comprises one or more panel fasteners which enable securing said front panel with said belt, and wherein said absorbent article is configured such that it may be secured and worn about the waist of a wearer in both an attached condition of said releasable attachments and in a released condition of said releasable attachments.

16. The absorbent article according to claim 15, wherein stretchable material is provided in at least one front or rear panel to thereby provide extensibility in a lateral direction of respective said panel.

17. The absorbent article according to claim 15, wherein when said front panel is attached to said respective belt portions in said retracted configuration of said belt portions, a substantially same waist size of said absorbent article may be generated as in when said front panel is attached to said belt portions in an extended configuration thereof, when they are joined to one-another by said belt fastener.

18. The absorbent article according to claim 15, wherein said one or more panel fasteners are arranged such that at least one fastener is located on said front panel at or near each opposite lateral region of said panel.

19. The absorbent article according to claim 15, wherein stretchable material is provided in said front panel such that the lateral width dimension of said front panel may be increased by at least one third upon extension of the front panel in the lateral direction.

20. The absorbent article according to claim 15, wherein said belt portions are made from nonwoven material capable of being securely engaged by a mechanical or adhesive belt fastener or panel fastener.

* * * * *